(12) United States Patent
Ishikawa et al.

(10) Patent No.: US 10,900,970 B2
(45) Date of Patent: Jan. 26, 2021

(54) IMMUNOCHROMATOGRAPHIC DEVICE REDUCED IN BACKGROUND NOISE AND METHOD FOR REDUCED BACKGROUND NOISE

(71) Applicant: Denka Company Limited, Tokyo (JP)

(72) Inventors: Osamu Ishikawa, Niigata (JP); Risa Kohiyama, Niigata (JP); Takashi Miyazawa, Niigata (JP)

(73) Assignee: Denka Company Limited, Tokyo (JP)

( * ) Notice: Subject to any disclaimer, the term of this patent is extended or adjusted under 35 U.S.C. 154(b) by 403 days.

(21) Appl. No.: 15/569,554

(22) PCT Filed: Apr. 27, 2016

(86) PCT No.: PCT/JP2016/063796
§ 371 (c)(1),
(2) Date: Oct. 26, 2017

(87) PCT Pub. No.: WO2016/174336
PCT Pub. Date: Nov. 3, 2016

(65) Prior Publication Data
US 2018/0095088 A1    Apr. 5, 2018

(30) Foreign Application Priority Data

Apr. 27, 2015    (JP) ................. 2015-090798

(51) Int. Cl.
*G01N 33/558* (2006.01)
*G01N 33/58* (2006.01)
*G01N 33/543* (2006.01)

(52) U.S. Cl.
CPC ......... *G01N 33/585* (2013.01); *G01N 33/543* (2013.01); *G01N 33/54366* (2013.01); *G01N 33/558* (2013.01)

(58) Field of Classification Search
CPC .................................................. G01N 33/558
(Continued)

(56) References Cited

U.S. PATENT DOCUMENTS 6,846,453 B1 * 1/2005 Uesaka ................. B01L 3/5023
422/402
2003/0017615 A1   1/2003 Sidwell et al.

FOREIGN PATENT DOCUMENTS

JP    08-094618 A     4/1996
JP    2004-536309 A  12/2004
JP    2013-228350 A  11/2013

OTHER PUBLICATIONS

International Search Report dated Jul. 19, 2016, in PCT/JP2016/063796.

(Continued)

*Primary Examiner* — Christopher L Chin
(74) *Attorney, Agent, or Firm* — Foley & Lardner LLP

(57) ABSTRACT

An object of the present invention is to improve visibility by reducing background noise in order to accurately detect the signal from a target substance in an immunochromatographic device. The immunochromatographic device comprises a membrane having a detection region, to which an antibody or antigen serving as a capturing substance capable of capturing a target substance is immobilized, for detecting the target substance by using an antigen or antibody labeled with a labeling carrier that is a colored particle to form a complex of the capturing substance-target substance-labeled antigen or antibody in the capturing substance-immobilized detection region on the device, based on color of the labeling carrier,
wherein a colorant having a color complementary to the color of the labeling carrier is allowed to be contained in a dry state in a constituent member of the device such that the
(Continued)

colorant is developed together with a specimen when the specimen is developed on the device.

6 Claims, 6 Drawing Sheets

(58) Field of Classification Search
USPC ..... 422/400, 401, 420, 425, 430; 435/287.7, 435/287.9, 970, 805, 810; 436/169, 514, 436/518, 530, 810
See application file for complete search history.

(56) References Cited

OTHER PUBLICATIONS

ImmunoAce® Flu, package insert, Oct. 2011, $10^{th}$ Ed., with English translation.
Nanotrap® IIR, instruction manual, Nov. 2014, $4^{th}$ Ed., with English translation.
Prime Check® Flu-RSV, package insert, Jan. 2013, $3^{rd}$ Ed., with English translation.
QuickNavi™-Flu, package insert, Nov. 2014, $13^{th}$ Ed., with English translation.

\* cited by examiner

No colorant

Colorant (yellow-green) is used

No colorant

Colorant (blue-green) is used

No colorant

Colorant (blue-green) is used

No colorant

Colorant (yellow-green) is used

IMMUNOCHROMATOGRAPHIC DEVICE REDUCED IN BACKGROUND NOISE AND METHOD FOR REDUCED BACKGROUND NOISE

CROSS-REFERENCE TO RELATED APPLICATIONS

This application is a National Stage application of PCT/JP2016/063796, filed Apr. 24, 2016, which claims priority from Japanese application JP 2015-090798, filed Apr. 27, 2015.

TECHNICAL FIELD

The present invention relates to improving visibility by reducing background noise in order to accurately detecting a signal from a target substance in an immunochromatographic device.

BACKGROUND ART

In an immunochromatographic device, a labeling carrier, which is developed together with a specimen, is an essential component in the detection method of the invention. Since the presence or absence of a target substance is principally detected based a colored image, the carrier itself displays a visible color. Because of this, the signal to be detected is affected by background noise of the same color and loses visibility. The loss of visibility has been a problem to be solved. To solve the problem, it has been proposed that a developing solution having a complementary color to that of a labeling carrier is used as a solution for extracting a target substance from a specimen and dispersing it (hereinafter referred to as a specimen extract) (Patent Literature 1). However, in this method, it is not considered that when an indefinite amount of specimen taken by e.g., a cotton swab is mixed with a specimen extract, a colorant component is also indefinitely diluted. The effect provided to a detection system significantly varies. In order to improve visibility by using the complementary relationship in color between the labeling carrier and the specimen extract, it is desirable that not only hue but also lightness and intensity are controlled. In this method, however, it is extremely difficult to deal with the indefinite amount of specimen taken.

In the meantime, test reagents, in which a single type of specimen extract is commonly used in a plurality of detection systems, are now widely used (Non Patent Literatures 1 to 4: QuickNavi (trademark)-Flu package insert/ImmunoAce (registered trade mark) Flu package insert/Prime Check (registered trade mark) Flu-RSV, package insert/Nano Trap (registered trade mark) IIR instruction manual). Although it is not limited to these existing products, the labeling carrier to be used is selected from many types of products different in color. It is principally impossible to develop a complementary color corresponding to all of the label carriers. Thus, adding a specific color to a specimen extract is contradictory to convenience, i.e., universal use of a reagent, and not reasonable as a choice.

CITATION LIST

Patent Literature

Patent Literature 1: JP Patent Publication (Kokai) No. 2013-228350

Non Patent Literature

Non Patent Literature 1: QuickNavi (trademark)-Flu package insert (revised in November, 2014 (13th edition))
Non Patent Literature 2: ImmunoAce (registered trade mark) Flu package insert (revised in October, 2011 (10th edition))
Non Patent Literature 3 Prime Check (registered trade mark) Flu-RSV, package insert (revised in January, 2013 (3rd edition))
Non Patent Literature 4: Nano Trap (registered trade mark) IIR instruction manual (November, 2014, 4th edition)

SUMMARY OF INVENTION

An object of the present invention is to improve visibility by reducing background noise caused by a labeling carrier of a labeled antibody or labeled antigen in order to accurately detect the signal from a target substance in an immunochromatographic device.

The present inventors intensively studied on a method for reducing background noise in an immunochromatographic device having a labeling carrier accumulated by using an antibody or antigen labeled with the labeling carrier to form an antigen-antibody complex in a detection region, the background noise caused by the remaining labeling carrier of the labeled antibody or labeled antigen on a membrane having the detection region of the immunochromatographic device.

The present inventors have found that a colorant having a color complementary to the color of a labeling carrier is arranged in a constituent member positioned upstream of a detection region in the device such that the colorant is developed together with a specimen and a labeling carrier when the specimen is developed, thereby enabling reduction in the intensity of the color of the labeling carrier on the membrane by the co-presence of the labeling carrier and the colorant on the membrane, more specifically, the colorant having a color complementary to the color of the labeling carrier, to reduce background noise. Based on the finding, the present invention has been accomplished.

More specifically, the present invention is as follows.

[1] An immunochromatographic device comprising a membrane having a detection region, to which an antibody or antigen serving as a capturing substance capable of capturing a target substance is immobilized, for detecting the target substance by using an antigen or antibody labeled with a labeling carrier that is a colored particle to form a complex of the capturing substance-target substance-labeled antigen or antibody in the capturing substance-immobilized detection region on the device, based on color of the labeling carrier, wherein a colorant having a color complementary to the color of the labeling carrier is allowed to be contained in a dry state in a constituent member of the device such that the colorant is developed together with a specimen when the specimen is developed on the device.

[2] The immunochromatographic device according to [1], wherein the constituent member in which the colorant having a color complementary to the color of the labeling carrier is allowed to be contained is a member arranged on the upstream side of the detection region.

[3] The immunochromatographic device according to [1] or [2], wherein the constituent member in which the colorant having a color complementary to the color of the labeling carrier is allowed to be contained is a sample pad.

[4] The immunochromatographic device according to any one of [1] to [3], wherein the colorant is a dye or a pigment.
[5] The immunochromatographic device according to any one of [1] to [3], wherein the colorant is a color particle.
[6] A method for reducing background noise in an immunochromatographic device, the device comprising
a membrane having a detection region, to which an antibody or antigen serving as a capturing substance capable of capturing a target substance is immobilized, for detecting the target substance by using an antigen or antibody labeled with a labeling carrier that is a colored particle to form a complex of the capturing substance-target substance-labeled antigen or antibody in the capturing substance-immobilized detection region on the device, based on color of the labeling carrier,
by allowing a colorant having a color complementary to the color of the labeling carrier to be contained in a dry state in a constituent member of the device; and
allowing the colorant to develop together with a specimen on the device when a specimen is developed on the device, thereby reducing the intensity of color of the background noise derived from the labeling carrier.
[7] The method for reducing background noise according to [6], wherein the constituent member in which the colorant having a color complementary to the color of the labeling carrier is allowed to be contained is a member arranged on the upstream side of the detection region.
[8] The method for reducing background noise according to [6] or [7], wherein the constituent member in which the colorant having a color complementary to the color of the labeling carrier is allowed to be contained is a sample pad.
[9] The method for reducing background noise according to any one of [6] to [8], wherein the colorant is a dye or a pigment.
[10] The method for reducing background noise according to any one of [6] to [8], wherein the colorant is a color particle.

Owing to the immunochromatographic device of the present invention or the method of the present invention, it is possible to reduce background noise and improve visibility of a detection signal in the immunochromatographic device, and accurately detect an antigen or antibody in a specimen.

The specification contains the disclosure of JP Patent Application No. 2015-090798, based on which the priority of the present application is claimed.

DESCRIPTION OF EMBODIMENTS

Now, the present invention will be more specifically described below.

Figure 1:
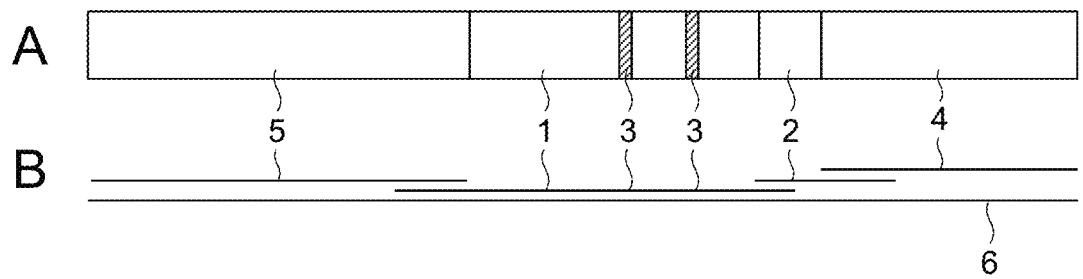
FIG. 1 shows a structure of the immunochromatographic device of the present invention.

FIG. 1 shows a preferable embodiment of an immunochromatographic device according to the present invention. The immunochromatographic device shown in FIG. 1 is constituted of constituent members: a membrane 1, a labeling reagent region 2, a detection region 3, a sample pad 4, an absorption zone 5 and a backing sheet 6. The members can be also called as materials or regions.

FIG. 1A is a top view and FIG. 1B is a sectional view. In the embodiment shown in the figures, the membrane 1 having two detection regions 3 formed therein, the absorption zone 5, the labeling reagent region 2 and the sample pad 4 are individually laminated on the backing sheet 6. As shown in the figures, one of the end portions of the absorption zone 5 is overlapped with one of the end portions of the membrane 1; the other end portion of the membrane 1 is overlapped with one of the end portions of the labeling reagent region 2; and the other end portion of the labeling reagent region 2 is overlapped with one of the end portions of the sample pad 4. With this structure, a continuous lateral-flow path is formed.

The membrane 1 is a member capable of immobilizing a capturing substance for capturing a target substance, and not preventing liquid from flowing in the horizontal direction. The membrane 1 is preferably formed of a porous thin film having a capillary action and a material capable of transporting a liquid and components dispersed in the liquid by absorbing and then developing them. Examples of the material for the membrane, include, but are not particularly limited to, cellulose, nitrocellulose, cellulose acetate, polyvinylidene difluoride (PVDF), a glass fiber, nylon and polyketone. Among them, nitrocellulose is preferable and a thin film of nitrocellulose is more preferable.

The labeling reagent region 2 is formed of a porous substrate containing labeled antibody being an antibody against the target substance and labeled with a labeling carrier. As a material for the substrate, a material generally used such as a glass fiber and a nonwoven fabric, can be employed. The substrate is preferably a pad having a thickness of about 0.3 mm to 0.6 mm in order to be impregnated with a large amount of labeled antibody.

The labeling carrier refers to a substance which forms a complex with a target substance and thereafter can be detected by some means. For example, an enzyme such as alkaline phosphatase and horseradish peroxidase, metallic colloid such as gold colloid, a particle such as a silica particle, a cellulose particle and a colored latex particle are mostly used. If a metallic colloidal particle or a color particle such as a colored latex particle is used, since these labeling reagents are aggregated to produce color, the color is measured. If an enzyme is used, operations for adding a substrate and terminating the reaction between the enzyme and the substrate are required in a measuring step. In contrast, if a metallic colloidal particle or a colored latex particle is used, such operations are not required. Recently, in an (examination) item such as influenza (virus) requiring a large number of examinations during the epidemic period, rapid measurement is carried out at clinical sites. Since a rapid test reagent used for this purpose is mostly handled by e.g., doctors, nurses and clinical laboratory technicians on site, further simplification of the measurement step is required. For the reason, a metallic colloidal particle or a colored latex particle easily handled is frequently used. As the colored latex particle, a colored latex particle using e.g., a polystyrene particle, is often used. In particular, when a colored latex particle is used, various types of particles different in color and size can be manufactured. Actually, many types of particles are commercially available. Since suitable particles can be selected in accordance with individual purposes, the number of cases employing colored latex particles has been increased. Furthermore, a method for detecting a plurality of target substances by using a plurality of latex particles different in color tone is proposed. The immunochromatographic device used in the present invention is desirably a device using a color particle such as a metallic colloidal particle or a colored latex particle as a labeling carrier. In the present invention, when the labeling carrier is a color particle, the color of the labeling carrier refers to the color of the particle itself, whereas when the labeling carrier is an enzyme, the color of a labeling carrier refers to the color produced by an enzymatic reaction.

The detection region 3 refers to a partial region (member) of the membrane to which a capturing substance for capturing a target substance is immobilized. In an immunochromatographic device for detecting an antigen, the target substance is the antigen and the capturing substance is an antibody. In this case, at least one of the detection region 3, to which an antibody for capturing an antigen is immobilized, is provided.

Note that, the number of the detection regions 3 and the number of types of labeled antibodies contained in the labeling reagent region 2 are not limited to one. If antibodies corresponding to a plurality of target substances to be detected are used, two or more antigens can be measured by a single immunochromatographic device. In the device of such a constitution, a mixture of labeled antibodies is contained in the labeling reagent region 2, the specific colors and concentrations of individual labeled antibodies and the mixing ratio of them are important elements since they complicate an object of the present invention.

The sample pad 4 is a member for adding dropwise a specimen or a sample prepared from a specimen, and made of a porous material having water absorbability. As the material, a material used in general, such as cellulose, a glass fiber and a nonwoven fabric, can be used. For subjecting a large amount of specimen to immunoassay, the material is preferably a pad having a thickness of about 0.3 mm to 1 mm. Note that, the sample pad and the labeling reagent region 2 are the areas just functionally divided and not necessarily formed of different materials. More specifically, a partial region of a sample pad may have a function as a labeling reagent region.

The absorption zone 5 is a member for absorbing components supplied to the membrane 1 and not involved in a reaction in the detection region 3. As the material, a filter paper and sponge having high water-holding property and formed of e.g., a natural polymer compound and a synthetic polymer compound generally used, can be used and a material having a high water absorbability is preferably used in order to accelerate development of a specimen.

The backing sheet 6 is a member to which all the members mentioned above, more specifically, the membrane 1, the sample pad 4, the labeling reagent region 2 and the absorption zone 5, are to be attached and immobilized with overlapped portions between them. The backing sheet 6 is not always necessary as long as these members can be arranged and immobilized at optimal intervals; however, the backing sheet is generally and preferably used in view of convenience for manufacturing and utilizing.

The immunochromatographic device of the present invention may have a control display region (member). The control display region is a site indicating that a test is carried out without fail. For example, the control display region is present downstream of the detection region. When a specimen sample passes through the detection region and reaches the control display region, a signal, e.g., color signal, is sent out. In the control display region, a material capable of binding to an antibody tagged with a labeling carrier may be immobilized or a reagent such as a pH indicator which changes color when a specimen sample reaches, may be immobilized. When the antibody tagged with a labeling carrier is a mouse monoclonal antibody, an anti-mouse IgG antibody may be used.

In the immunochromatographic device having a structure shown in FIG. 1, a liquid specimen is added dropwise to the sample pad. The specimen then passes through a porous flow path, which is formed by continuously connecting the sample pad, labeling reagent region, membrane, detection region and absorption zone. Thus, in the embodiment, all of the constituent members constitute a specimen migration region. Depending upon the material and form of the constituent member, a specimen may possibly run along the interface of the members without permeating into the inside of the members; however, the specimen migration region defined in the specification may be the inside of members or the interface between members. Accordingly, an immunochromatographic device having the aforementioned constitution is included in the scope of the specification.

The specimen supplied to the sample pad is horizontally developed by a capillary action sequentially toward the labeling reagent region, membrane and absorption zone. In labeling reagent region, a labeled antibody is released into a liquid simultaneously with development of the specimen sample and then developed toward the membrane. If an antigen is present in the specimen sample, the antigen is specifically captured by a capturing antibody in the detection region of the membrane and the antigen specifically reacts with the labeled antibody to form a complex. In this manner, in the detection region, the antigen is sandwiched by the antibodies to form a complex of the capturing substance-antigen (target substance)-labeled antibody. The labeled antibody-antigen complex can be measured based on the presence of the labeling carrier as an indicator in the detection region. For example, when the labeling carrier is a color particle such as a metallic colloidal particle or a colored latex particle, if an antigen is present, color particles accumulate in the detection region, with the result that the detection region produces color. Thus, the antigen can be detected by detecting the color visually or by an optical measuring device. Note that, in the present invention, a specimen flows from a sample pad toward the absorption zone. Based on the direction of the flow, the region close to the sample pad is called as the upstream region and the region close to the absorption zone is called as the downstream region. For example, in the device having the structure shown in FIG. 1, the sample pad and labeling reagent region are arranged upstream of the detection region.

The description in the above relates to the case where an antigen in a specimen is detected by using a labeled antibody. The antibody against the aforementioned antigen in a specimen can be detected by using an antigen as a capturing substance, and a labeled antigen as a labeled substance. In this case, an antigen to which an antibody (a target substance) is to be bound and labeled with a labeling carrier is contained in the labeling reagent region and the antigen capturing the antibody (the target substance) is immobilized as a capturing substance in the detection region.

The present invention provides a method for improving visibility of a detection signal by reducing background noise, in an immunochromatographic device. The background noise refers to noise derived from color of labeling carrier of the remaining labeled antibody or labeled antigen on a membrane when the labeled antibody or labeled antigen is developed on a device by capillary phenomenon. The labeled antibody or labeled antigen present on the detection region on the membrane is hard to see by the noise. The presence or absence of a target substance by chromatographic device in the case where a labeling carrier is a color particle, is determined by visual observation of color of the labeling carrier of a labeled antibody or a labeled antigen captured and accumulated on the detection region. Thus, if the background noise is high, the labeled antibody or labeled antigen in the detection region is hard to distinguish and sometimes determination may become difficult. In particular, when the target substance is present in a trace amount, the labeled antibody in the detection region cannot be observed clearly and cannot be read accurately, with the result that an erroneous judgment may be made. Since the level of the background noise varies depending upon the amount of labeled antibody or labeled antigen, the level of the background noise is the highest immediately after releasing from the labeling reagent region and tends to gradually decrease with the passage of time. Accordingly, in order to make a rapid detection at clinical sites, it is useful to quickly reduce the high level of background immediately after development.

In the present invention, the colorant having a color complementary to the color of the labeling carrier is allowed to be contained in a dry state in a constituent member of an immunochromatographic device. Owing to this, a specimen supplied to a sample pad is developed toward a membrane. In accordance with this, a labeled antibody or labeled antigen is re-eluted from the labeling reagent region and developed towards a membrane; at the same time a colorant having a complementary color to the labeling carrier is re-eluted and developed. As a result of co-presence of the labeling carrier and the colorant on the membrane, background noise derived from the labeled antibody or labeled antigen is reduced.

The constituent member in which a colorant having a complementary color to the labeling carrier is allowed to be contained is desirably a member arranged upstream of the detection region. Examples of the member arranged upstream of the detection region include all members present upstream of the detection region; more specifically, the membrane, labeling reagent region and sample pad (which are positioned upstream of the detection region) are mentioned. Separately from these, a member containing a colorant may be provided at an arbitrary position upstream of the detection region. The constituent member containing a colorant is more desirably a sample pad.

As a method for allowing a colorant to be contained in a constituent member, any technique known in the art such as pouring, dipping, spraying, thermal spraying and evaporation may be used as long as the colorant can be re-eluted with a specimen extract; however, in view of accuracy and convenience, a method of applying a colorant by spraying followed by drying is desirable. In this application, the "dry state" refers to being dried and not wet to the extent that no disadvantage is provided in view of performance and manufacturing. In a precise sense, e.g., an amorphous state (glass state) may be mentioned.

As the colorant having a complementary color to the labeling carrier of the present invention, a dye or pigment known in the art can be used. In addition, not only a substance displaying color itself but also e.g., a color particle to which a colorant is attached, bound or added, can be used. As the particle to be colored, a resin particle such as a polystyrene particle or a latex particle, can be used. The colorant to be used desirably has a complementary color to the overall color displayed by labeled antibodies or labeled antigens used in the detection system.

The "complementary color" in the present invention refers to a hue which reduces intensity of the color of a labeling carrier of a labeled antibody or labeled antigen when mixed with the labeled antibody or labeled antigen, and produces color close to an achromatic color. In the color wheel, a color located at an angular difference of 120 to 180° from the color of a labeling carrier of a labeled antibody or labeled antigen has the effect. Since the effect is higher as the angular difference is close to 180°, a color located at an angular difference within the range of 165 to 180° is more desirable. Generally, a "complementary color" refers to a color located at an angular difference of 180° in the color wheel, in short, the color located diametrically opposite; however, the "complementary color" in the present invention includes a color located at an angular difference within the range of 120 to 180° in the color wheel. As the color wheel, e.g., the PCCS color wheel (color combination system, Nippon Shikiken) of 24 hues, the Munsell color wheel based on the Munsell color system, and the Ostwald color wheel based on the Ostwald color system, are known. In the present invention, the "complementary color" may be based on any one of the color wheels. Accordingly, the "complementary color" in the present invention includes a complementary color located diametrically opposite to a predetermined color in a color wheel such as PCCS color wheel, Munsell color wheel or Ostwald color wheel and also includes "adjacent hue" and "similar hue" having hue difference of 1 to 3 from the complementary color. The complementary color on the PCCS color wheel is a psychological complementary color. The psychological complementary color refers to the color of a complementary afterimage seen when a person stares at a chromatic color. Complementary colors on the Munsell color wheel and the Ostwald color wheel are physical complementary colors. The physical complementary colors refer to colors producing an achromatic color when mixed. In the present invention, the "complementary color" includes psychological complementary colors as well as physical complementary colors.

For example, in the case where a red labeling carrier such as a red polystyrene latex particle is used, a complementary color to red is blue to green. Thus, a blue-green colorant can be used as a complementary colorant. In the case where a blue labeling carrier such as a blue polystyrene latex particle is used, a complementary color to blue is orange to red. Thus, an orange colorant can be used as a complementary colorant. A plurality of labeling carriers different in color may be used. When a red particle and a blue particle are used in combination, a yellow-green colorant can be used. Colorants may be mixed, adjusted to a desired color and then used.

Owing to use of a complementary colorant to a labeling carrier, the color intensity of the label carrier remaining on the membrane decreases; the membrane looks white and the color contrast between the labeling carrier and the membrane in the detection region increases; and the color of the labeling carrier in the detection region is clearly seen.

In the present invention, an immunochromatographic device using a red labeling carrier alone and an immunochromatographic device using a blue labeling carrier alone are called as a red single color system immunochromatographic device and a blue single color system immunochromatographic device, respectively. A plurality of labeling carriers different in color may be used. The immunochromatographic device using a red particle and a blue particle in combination is called as a red and blue mixed color system immunochromatographic device.

Examples of the colorant to be used in the red single color system immunochromatographic device include blue-green colorant such as Fast Green FCF and Alizarin Cyanine Green F, Blue colorants such as Brilliant Blue FCF, Indigo Carmine, Xylene Cyanol FF and Bromophenol Blue. Examples of the colorant to be used in the red and blue mixed color system immunochromatographic device include a yellow-green colorant, i.e., light green SF Yellow and a yellow-green colorant, i.e., a mixture of Alizarin Cyanine Green F and tartrazine. Examples of the colorant to be used in the blue single color system immunochromatographic device include yellow tartrazine.

There was a conventional method in which a colorant is previously added to a specimen extract (JP Patent Publication (Kokai) No. 2013-228350). However, since a specimen, i.e., a biological sample, is indefinitely taken by e.g., swab, a specimen is sometimes excessively taken, with the result that a specimen extract fails to be developed well and a colorant remains on a membrane, increasing background noise. In addition to this problem, there is another problem in that the specimen extract is diluted with an excessive amount of specimen, the color of the colorant is lightened. The factors of these changes are derived from the fact that the amount of specimen extract to be added to a test reagent (also called as a kit or a device) is defined although the collection amount of specimen is indefinite. In the present invention, since a colorant is previously arranged in the structure member in an immunochromatographic device, the color is not influenced by the amount of specimen to be taken. More specifically, in contrast to the prior art, the predetermined amount of colorant is contained in a reagent and development is carried out with a predetermined amount of specimen extract.

Since high or low of background noise is closely related to the amount of labeling carrier, the level of background noise changes with the passage of time from the time of the dropwise addition of a specimen extract to the time of completion of a reaction. In a conventional method in which a colorant is added to a specimen extract, since a colorant solution having a constant color-tone is developed in any time point between the beginning of development having high background noise and the time of termination having low background noise, the embodiment of the conventional method is not ideal. Whereas, in the method of the present invention, the concentration of a colorant is high in the beginning of the development and low in the time of termination, similarly to the labeling carrier. The embodiment of the invention is in conjunction with a change of the background noise with time.

In the method of the present invention, a biological sample to be measured is preferably a specimen containing a substance derived from the mucosa of a living body. Examples thereof include a nasopharyngeal mucosa-derived specimen and an oral mucosa-derived specimen such as sputum, saliva, pharyngeal swab, nasal swab, nasal aspirate, keratoconjunctival swab and stool specimen.

In the method of the present invention, a target substance to be measured is an antigen or antibody that can be measured by immunoassay, more specifically, assay using an antigen-antibody reaction. As the antigen, any antigen may be used so long as it can produce an antibody. The examples are a protein, a polysaccharide and a lipid. Protozoa, fungus, bacterium, mycoplasma, rickettsia, chlamydia and a virus that contain these substances can also be measured.

The present invention includes an antigen or antibody detection kit containing the aforementioned immunochromatographic device having a colorant. The kit contains a reagent for taking a specimen, a device for taking a specimen and a brochure other than the immunochromatographic device.

Now, the present invention will be more specifically described below based on Examples below; however, the present invention is not limited to the following Examples.

[Example 1] Preparation of Red and Blue Mixed Color System Immunochromatographic Device 1. Preparation of Labeled Anti-Influenza A Virus Antibody (Labeled Anti-Type A Antibody)

An anti-influenza A virus monoclonal antibody was dialyzed against a buffer solution (pH6.0) and then mixed with red polystyrene latex particles to react them. Subsequently, EDAC (N-(3-dimethylaminopropyl)-N'-ethylcarbodiimide hydrochloride) was added so as to obtain a final concentration of 0.1% and reacted for two hours. After washing, the mixture was suspended in 5 mM Tris, 0.04 (W/V) % BSA (bovine serum albumin) and the latex particles were dispersed by an ultrasonic dispersion device.

2. Preparation of Labeled Anti-Influenza B Virus Antibody (Labeled Anti-Type B Antibody)

An anti-influenza B virus NP monoclonal antibody was dialyzed against a buffer solution (pH6.0) and then mixed with blue polystyrene latex particles to react them. Subsequently, EDAC was added so as to obtain a final concentration of 0.1% and reacted for two hours. After washing, the mixture was suspended in 5 mM Tris, 0.04 (W/V) % BSA (bovine serum albumin) and the latex particles were dispersed by an ultrasonic dispersion device.

3. Preparation of Labeled Antibody Pad

The labeled anti-type A antibody and labeled anti-type B antibody prepared in the above Sections 1 and 2 were added in equal amounts and stirred at room temperature and 150 rpm for 5 minutes. The labeled antibody mixture was sprayed onto the whole surface of cellulose nonwoven cloth reel having a width of 10 mm, by using a positive-pressure spray apparatus. After spraying, the nonwoven cloth was dried by applying hot air of 50° C. for 10 minutes to prepare a labeled antibody pad.

4. Preparation of Anti-Influenza A Virus Antibody for Immobilization to Membrane (Anti-Type A Antibody for Immobilization)

A purified anti-influenza A virus NP monoclonal antibody different from the antibody used in Section 1 was dialyzed against an immobilization solution (10 mM Tris-HCl (pH7.5)). After dialysis, 0.22 μm filtration was carried out and dilution with the immobilization solution was carried out to prepare the anti-type A antibody for immobilization.

5. Preparation of Anti-Influenza B Virus Antibody (Anti-Type B Antibody for Immobilization) for Immobilization A purified anti-influenza B virus NP monoclonal antibody different from the antibody used in Section 2 was dialyzed against an immobilization solution (10 mM Tris-HCl (pH7.5)). After dialysis, 0.22 μm-filtration was carried out and dilution with the immobilization solution was carried out to prepare the anti-type B antibody for immobilization.

6. Preparation of Membrane on which Antibodies are Immobilized

As a membrane, a nitrocellulose membrane sheet (white) of 3 cm (width)×10 cm (length) was used. The anti-type A antibody for immobilization was linearly applied to the position on the membrane at a distance of 8 mm from one of the ends in the longitudinal direction (this end was defined as the upstream end and the opposite end was defined as the downstream end); the anti-type B antibody for immobilization was linearly applied to the position at a distance of 10 mm and an anti-mouse IgG antibody was linearly applied to the position at a distance of 12 mm, by using a positive-pressure spray apparatus to prepare detection regions. After application, the membrane was dried by applying hot air of 45° C. for 10 minutes.

7. Preparation of Pad Impregnated with a Red and Blue Mixed Color System Colorant A colorant solution (0.001% Alizarin Cyanine Green F, 0.002% tartrazine) was prepared by blending colorants so as to obtain yellowish green color, and sprayed onto the whole surface of polyester nonwoven cloth reel having a width of 20 mm by using a positive-pressure spray apparatus. After spraying, the nonwoven cloth was dried by applying hot air of 50° C. for 10 minutes to prepare a colorant-impregnated pad.

8. Preparation of Immunochromatographic Device for Detecting Influenza Viruses

Figure 2:
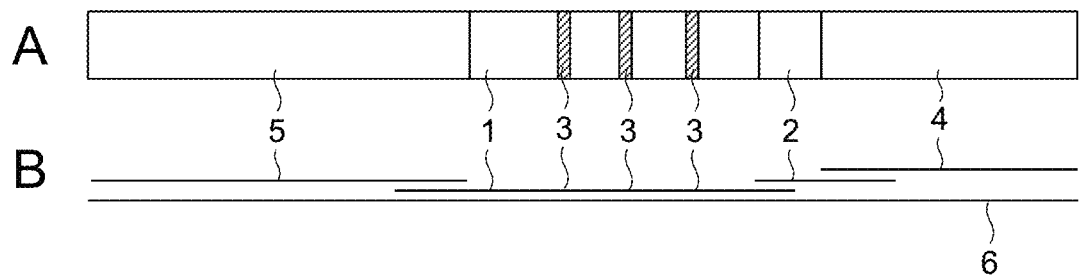
FIG. 2 shows a structure of an immunochromatographic device for detecting influenza virus used in Examples.

The structure of an immunochromatographic device for detecting influenza viruses was the same as shown in FIG. 2. The labeled antibody pad 2 (prepared in Section 3), membrane 1 for immobilizing an antibody, having detection regions 3 (prepared in Section 6), colorant-impregnated pad 4 (prepared in Section 7) and other members (the backing sheet 6, the absorption zone 5) were adhered. The resultant construct was cut into pieces (5 mm) along the longitudinal direction to prepare the immunochromatographic devices shown in FIG. 2.

[Example 2] Preparation of Red Single Color System Immunochromatographic Device

1. Preparation of Labeled Anti-*Mycoplasma pneumoniae* Antibody (Labeled Anti-Mp Antibody)

An anti-*Mycoplasma pneumoniae* monoclonal antibody was dialyzed against a buffer solution (pH6.0) and then mixed with red polystyrene latex particles to react them. Subsequently, EDAC (N-(3-dimethylaminopropyl)-N'-ethylcarbodiimide hydrochloride) was added so as to obtain a final concentration of 0.1% and reacted for two hours. After washing, the mixture was suspended in 5 mM Tris, 0.04 (W/V) % BSA (bovine serum albumin) and the latex particles were dispersed by an ultrasonic dispersion device.

2. Preparation of Labeled Antibody Pad

The labeled anti-Mp antibody prepared in Section 1 was splayed onto the whole surface of cellulose nonwoven cloth reel having a width of 10 mm by using a positive-pressure spray apparatus. After spraying, the nonwoven cloth was dried by applying hot air of 50° C. for 10 minutes to prepare a labeled antibody pad.

3. Preparation of Anti-*Mycoplasma pneumoniae* Antibody (Anti-Mp Antibody for Immobilization) for Immobilization to Membrane A purified anti-*Mycoplasma pneumoniae* monoclonal antibody different from the antibody used in Section 1 was dialyzed against an immobilization solution (10 mM Tris-HCl (pH7.5)). After dialysis, 0.22 μm-filtration was carried out and dilution with the immobilization solution was carried out to prepare the anti-Mp antibody for immobilization.

4. Preparation of Membrane on which Antibodies are Immobilized

As a membrane, a nitrocellulose membrane sheet (white) of 3 cm (width)×10 cm (length) was used. The anti-Mp antibody for immobilization was linearly applied to the position on the membrane at a distance of 9 mm from one of the ends in the longitudinal direction (this end was defined as the upstream end and the opposite end was defined as the downstream end); and an anti-mouse IgG antibody was linearly applied to the position on the membrane at a distance of 12 mm, by using a positive-pressure spray apparatus to prepare detection regions. After application, the membrane was dried by applying hot air of 45° C. for 10 minutes.

5. Preparation of Pad Impregnated with a Red Single Color System Colorant

A colorant solution (0.001% Fast Green FCF) displaying blue-green was prepared and sprayed onto the whole surface of polyester nonwoven cloth reel having a width of 20 mm by using a positive-pressure spray apparatus. After spraying, the nonwoven cloth was dried by applying hot air of 50° C. for 10 minutes to prepare a colorant-impregnated pad.

6. Preparation of Immunochromatographic Device for Detecting *Mycoplasma pneumoniae*

The structure of an immunochromatographic device for detecting *Mycoplasma pneumoniae* was the same as shown in FIG. 2 except that a single detection region was used. The labeled antibody pad (prepared in Section 2), membrane on which antibodies are immobilized (prepared in Section 4), colorant-impregnated pad (prepared in Section 5) and other members (backing sheet, absorption zone) were adhered. The resultant construct was cut into pieces (5 mm) along the longitudinal direction to prepare the immunochromatographic devices shown in FIG. 2.

[Example 3] Verification of Background Noise Reduction in the Presence or Absence of Colorant 1. Verification in Red and Blue Mixed Color System Immunochromatographic Device (Red and Blue Mixed Color Detection System)

An immunochromatographic device according to Example 1 employing a sample pad previously prepared by applying a yellow-green colorant followed by drying, and an immunochromatographic device according to Example 1 employing a sample pad having no coating, were prepared.

A specimen extract was separately added dropwise to the device employing a sample pad previously prepared by applying a yellow-green colorant followed by drying, and the device employing a sample pad having no coating. Three minutes later, the backgrounds of the membranes were compared (see, FIG. 3).

Figure 3:
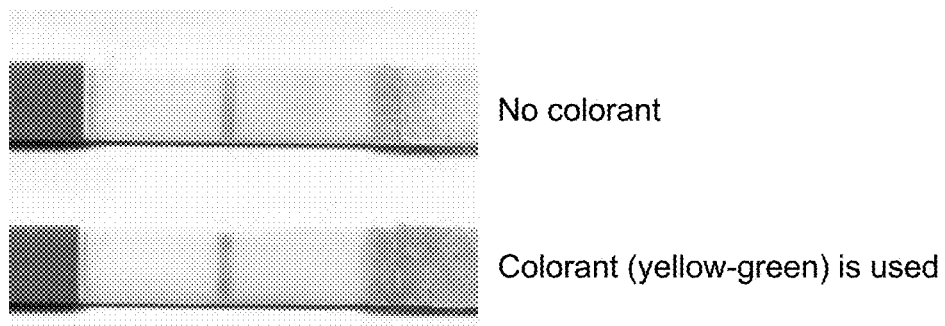
FIG. 3 shows the results of verification of background noise reduction in the presence or absence of a colorant.

As shown in FIG. 3 and Table 1, the membrane of the device using a sample pad impregnated with a colorant (FIG. 3, lower figure) looks white compared to the device containing no colorant. From this, it was found that the background noise was reduced and the color in the detection region was clearly seen.

2. Verification in Red Single Color System Immunochromatographic Device (Red Ssingle Color Detection System)

An immunochromatographic device according to Example 2 employing a sample pad previously prepared by applying a blue-green colorant, followed by drying, and an immunochromatographic device according to Example 2 employing a sample pad having no coating were prepared.

A specimen extract (containing inactivated and diluted *Mycoplasma pneumoniae* antigen) was separately added dropwise to the device using a sample pad previously prepared by applying a blue-green colorant, followed by drying, and the device employing a sample pad having no coating. Three minutes later, the backgrounds of the membranes were compared (see, FIG. 4).

Figure 4:
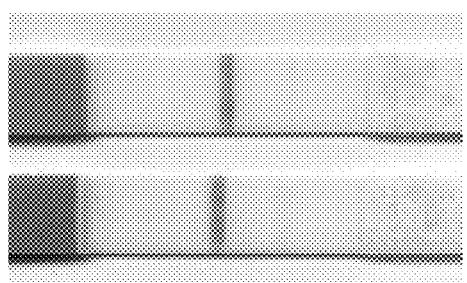
FIG. 4 shows the results of verification by a red single color system immunochromatographic device.

As shown in FIG. 4 and Table 1, the membrane of the device employing a sample pad impregnated with a colorant (FIG. 4, lower figure) looks white compared to the device containing no colorant. From this, it was found that the background noise was reduced and the color in the detection region was clearly seen.

TABLE 1

|  | Detection system | |
| --- | --- | --- |
|  | Red single color detection system | Red/blue mixed color detection system |
| No colorant | Control 1 | Control 2 |
| Colorant-impregnated pad | B.G. is lower than Control 1 | B.G. is lower than Control 2 |

[Example 4] Verification of Background Noise when a Common Specimen Extract is Used An immunochromatographic device according to Example 1 (red and blue mixed color system immunochromatographic device, devices Nos. 1 to 4) employing a sample pad previously prepared by applying a yellow-green colorant followed by drying (device No. 2), and immunochromatographic devices according to Example 1 employing a sample pad having no coating (device Nos. 1, 3 and 4) were prepared. An immunochromatographic device (red single color system immunochromatographic device, devices Nos. 5 to 8) according to Example 2 employing a sample pad previously prepared by applying a blue-green colorant followed by drying (device No. 6), and immunochromatographic devices according to Example 2 (device Nos. 5, 7 and 8) employing a sample pad having no coating, were prepared.

A colorless specimen extract was added dropwise to the device (device No. 2) employing a sample pad prepared by applying a yellow-green colorant followed by drying, and the device (device No. 6) employing a sample pad prepared by applying a blue-green colorant followed by drying. With respect to the devices (device Nos. 1, 3 and 4) according to Example 1 employing a sample pad having no coating, a colorless specimen extract (to device No. 1 (control 1)), a specimen extract containing a yellow-green colorant (to device No. 3) or a specimen extract containing a blue-green colorant (to device No. 4) were added dropwise. With respect to the devices according to Example 2 (device Nos. 5, 7 and 8) employing a sample pad having no coating, a colorless specimen extract (to device No. 5 (control 2)), a specimen extract containing a yellow-green colorant (to device No. 7) or a specimen extract containing a blue-green colorant (to device No. 8) were added dropwise. Three minutes later, the background noise levels of the membranes of individual devices were compared.

Figure 5:
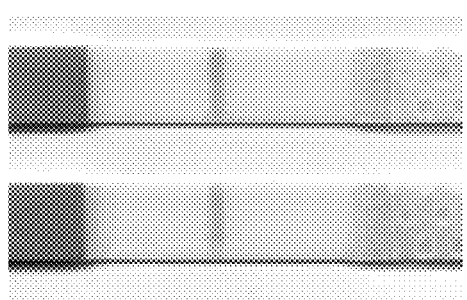
FIG. 5 shows the results of verification of background noise when a common specimen extract was used (red and blue mixed color system immunochromatographic device).

As is shown in Table 2, in the red single color system (red single color detection system) immunochromatographic device (device No. 8) using a specimen extract containing a blue-green colorant, background noise was low compared to control 2. In the red and blue mixed color system (red and blue mixed color detection system) immunochromatographic device (device No. 4) using the same specimen extract, the bluish color of the background was high compared to control 1, indicating that noise level was higher. FIG. 5 shows the background of device No. 4. FIG. 5 (upper figure) shows the result of device No. 1 (control 1) and FIG. 5 (lower figure) shows the result of device No. 4. FIG. 5 shows that the bluish color of the background of device No. 4 is high.

Figure 6:
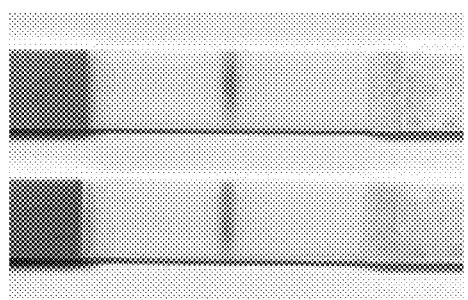
FIG. 6 shows the results of verification of background noise when a common specimen extract was used (red single color system immunochromatographic device).

Similarly, in the red and blue mixed color system (red and blue mixed color detection system) immunochromatographic device (device No. 3) using a specimen extract containing a yellow-green colorant, the background noise is low compared to control 1. In the red single color system (red single color detection system) immunochromatographic device (device No. 7) using the same specimen extract, a background noise improving effect was not obtained. FIG. 6 shows the background of device No. 7. FIG. 6 (upper figure) shows the result of device No. 5 (control 2) and FIG. 6 (lower figure) shows the result of device No. 7. FIG. 6 shows that the density of the background of device No. 7 is indistinguishable from the density of the background of device No. 5 (control 2).

More specifically, if a specimen extract containing a colorant prepared in accordance with either one of the detection systems is used in the other detection system, an anticipated effect is not provided and further original performance of the specimen extract may deteriorate. It is shown that the same specimen extract cannot be used in common.

In the method of the present application, an anticipated background noise reduction effect was obtained in either one of the detection systems by using the same colorless specimen extract in common.

TABLE 2

| Implementation conditions | | | | |
| --- | --- | --- | --- | --- |
|  | Sample pad | Specimen extract | Result | Device No. |
| Red/blue mixed detection system (Example 1) | No colorant | No colorant | Control 1 | 1 |
|  | Yellow-green colorant (method of the present application) | No colorant | B.G. was better than control 1 | 2 |
|  | No colorant | Yellow-green colorant (conventional method) | B.G. was better than control 1 | 3 |
|  | No colorant | Blue-green colorant (conventional method) | B.G. was worse than control 1 | 4 |
| Red single detection system (Example 2) | No colorant | No colorant | Control 2 | 5 |
|  | Blue-green colorant (method of the present application) | No colorant | B.G. was better than control 2 | 6 |
|  | No colorant | Yellow-green colorant (conventional method) | Not effective in improving B.G. | 7 |
|  | No colorant | Blue-green colorant (conventional method) | B.G. was better than control 2 | 8 |

[Example 5] Verification of Effect of Variation of Collection Amount of Specimen on Background Noise 1. Effect of Collection Amount of Specimen in Conventional Method An immunochromatographic device according to Example 2 employing a sample pad to which no colorant was applied, was prepared. A specimen extract (colorant setting amount/relative amount 1), to which an optimum amount of colorant was added, was added dropwise, as a control. In a simulation of a case where a large amount of specimen is taken, the aforementioned colorant containing specimen extract, to which a colorless pseudo specimen was added in a predetermined amount, was added dropwise and a test was carried out. Three minutes later, the background noise levels of membranes in individual devices were compared.

2. Effect of Collection Amount of Specimen in the Method of the Present Invention In the immunochromatographic device according to Example 2, a sample pad (colorant setting amount/relative amount 1), which was previously prepared by applying a blue-green colorant, followed by drying, was prepared, and a colorless specimen extract was added dropwise and used as a control. In a simulation of a case where a large amount of specimen is taken, a specimen extract, to which a colorless pseudo specimen was mixed in a predetermined amount, was added dropwise and a test was carried out. Three minutes later, the background noise levels of membranes in individual devices were compared.

As shown in Table 3, in a conventional method, as the collection amount of specimen increases, the amount of colorant supplied by dripping decreases, suggesting that the improving effect for red background noise derived from a labeled antibody decreases. In contrast, in the method of the present invention, it is shown that the amount of colorant developed in the detection system is not changed and a certain effect is always exerted.

TABLE 3

| Collection amount of specimen | Conventional method | | | Method of invention | | |
| --- | --- | --- | --- | --- | --- | --- |
| | Proper amount | Large | Excessive | Proper amount | Large | Excessive |
| Predetermined amount of colorant (relative value) | 1 | 1 | 1 | 1 | 1 | 1 |
| Amount of colorant (relative value) incorporated | 1 | 0.75 | 0.5 | 1 | 1 | 1 |
| Result | Control | B.G. is red | B.G. is red | Control | Equivalent to control | Equivalent to control |

INDUSTRIAL APPLICABILITY

An antigen and antibody in the specimen can be accurately detected by using the immunochromatographic device of the present invention.

REFERENCE SIGNS LIST

1 Membrane
2 Labeling reagent region
3 Detection region
4 Sample pad
5 Absorption zone
6 Backing sheet All publications, patent publications and patent applications cited in the specification are incorporated herein in their entirety by reference.

The invention claimed is:

1. An immunochromatographic device comprising
a membrane having a detection region, to which an antibody or antigen serving as a capturing substance capable of capturing a target substance is immobilized, for detecting the target substance by using an antigen or antibody labeled with a labeling carrier that is a colored particle to form a complex of the capturing substance-target substance-labeled antigen or antibody in the capturing substance-immobilized detection region on the device, based on color of the labeling carrier,
wherein a colorant having a color complementary to the color of the labeling carrier is allowed to be contained in a dry state in a sample pad arranged on an upstream side of the detection device such that the colorant is developed together with a specimen when the specimen is developed on the device.

2. The immunochromatographic device according to claim 1, wherein the colorant is a dye or a pigment.

3. The immunochromatographic device according to claim 1, wherein the colorant is a color particle.

4. A method for reducing background noise in an immunochromatographic device, the device comprising
a membrane having a detection region, to which an antibody or antigen serving as a capturing substance capable of capturing a target substance is immobilized, for detecting the target substance by using an antigen or antibody labeled with a labeling carrier that is a colored particle to form a complex of the capturing substance-target substance-labeled antigen or antibody in the capturing substance-immobilized detection region on the device, based on color of the labeling carrier,
the method comprising
allowing a colorant having a color complementary to the color of the labeling carrier to be contained in a dry state in a sample pad arranged on an upstream side of the detection region of the device; and
allowing the colorant to develop together with a specimen on the device when a specimen is developed on the device, thereby reducing the intensity of color of the background noise derived from the labeling carrier.

5. The method for reducing background noise according to claim 4, wherein the colorant is a dye or a colorant.

6. The method for reducing background noise according to claim 4, wherein the colorant is a color particle.

* * * * *